United States Patent [19]
Robinson

[11] 4,123,703
[45] Oct. 31, 1978

[54] MICROWAVE METHOD OF AND APPARATUS FOR FLAW DETECTION

[75] Inventor: Lloyd A. Robinson, Mountain View, Calif.

[73] Assignee: SRI International, Menlo Park, Calif.

[21] Appl. No.: 830,151

[22] Filed: Sep. 2, 1977

[51] Int. Cl.² ............................................ G01R 27/04
[52] U.S. Cl. .................................................. 324/58.5 B
[58] Field of Search ..................... 324/58.5 B, 58.5 A, 324/58.5 R

[56] References Cited

U.S. PATENT DOCUMENTS

| 3,532,973 | 10/1970 | Feinstein et al. | 324/58.5 B |
| 3,715,667 | 2/1973 | Nicolson | 324/58.5 B |
| 3,789,296 | 1/1974 | Caruso, Jr. et al. | 324/58.5 B |

FOREIGN PATENT DOCUMENTS 204,393  3/1971  U.S.S.R. .............................. 324/58.5 B

*Primary Examiner*—Stanley T. Krawczewicz
*Attorney, Agent, or Firm*—Victor R. Beckman

[57] ABSTRACT

A microwave flaw detector system and method are disclosed which include the use of a pair of parallel strip transmission lines which are located a parallel spaced distance from the surface of the test, or work, piece. The strip transmission lines are capable of supporting first and second orthogonal transmission modes, and means are included for supplying the same with a signal of the first mode. The strip transmission lines are located adjacent the surface of an object to be tested for flaws, and may be moved relative thereto for scanning the surface thereof for flaws. The test piece constitutes one ground plane for the pair of current-carrying strips within which return currents flow in a direction opposite to the strip currents. When a surface flaw on the test piece perturbs the ground plane current in the test piece under one strip, some of the power in the test piece is converted to a second mode orthogonal to the incident-mode current. Detector circuitry responsive only to the second mode signals is connected to the strip lines to provide an indication of detected surface flaws.

13 Claims, 7 Drawing Figures

MICROWAVE METHOD OF AND APPARATUS FOR FLAW DETECTION

ORIGIN OF INVENTION

The invention herein described was made in the course of or under a contract or subcontract thereunder, with the U.S. Army Materials and Mechanics Research Center, Watertown, Mass.

BACKGROUND OF THE INVENTION

Surface flaw detection apparatus and method which energize the surface of a test piece with energy of one mode and detect energy of an orthogonal mode which results from perturbation of the incident current in the presence of a surface flaw are well known as disclosed in an article by R. J. Hruby and L. Feinstein, "A Novel Nondestructive, Noncontacting Method of Measuring the Depth of Thin Slits and Cracks in Metals", *Rev. Sci. Insts.*, Vol. 41, No. 5, pp 679–683 (May 1970), and in U.S. Pat. No. 3,532,973, issued Oct. 6, 1970, entitled, "Microwave Flaw Detector", by L. Feinstein and R. J. Hruby. With such prior art arrangements surface illumination of the test piece with microwave energy is provided by a transmitting/receiving horn. Orthogonal mode signals produced as a result of the transmitted signal are received by the horn and provide an indication of surface flaws. The horn, however, is capable of illuminating only a small surface area, on the order of 2 cm in diameter, and extensive mechanical scanning of the horn relative to the total surface area of interest is required. With the present invention, using parallel strip transmission lines, an extended linear area may be covered, thereby greatly reducing the scanning necessary for inspection of the total surface area of interest.

SUMMARY OF THE INVENTION

An object of this invention is the provision of improved method and apparatus for microwave detection of surface flaws which cover an extended elongated area of the test object to reduce mechanical scanning required in the detection of flaws.

An object of this invention is the provision of a microwave coupled stripline surface flaw detecting method and apparatus which may be readily adapted for inspection of flat or curved surfaces.

The above and other objects and advantages are achieved by use of a pair of parallel strip transmission lines formed for positioning adjacent the test piece surface under investigation. The strip transmission lines, which are adapted to support first and second orthogonal transmission modes, are supplied with a signal of the first mode. Second orthogonal mode signals produced as the result of surface flaws adjacent the lines are received by the strip transmission lines and detected by detecting means responsive to said second mode signals and unresponsive to the transmitted first mode signals.

BRIEF DESCRIPTION OF THE DRAWINGS

The invention, together with further objects and advantages thereof will be better understood from the following description considered with the accompanying drawings. In the drawings, wherein like reference characters refer to the same parts in the several views.

Figure 1:
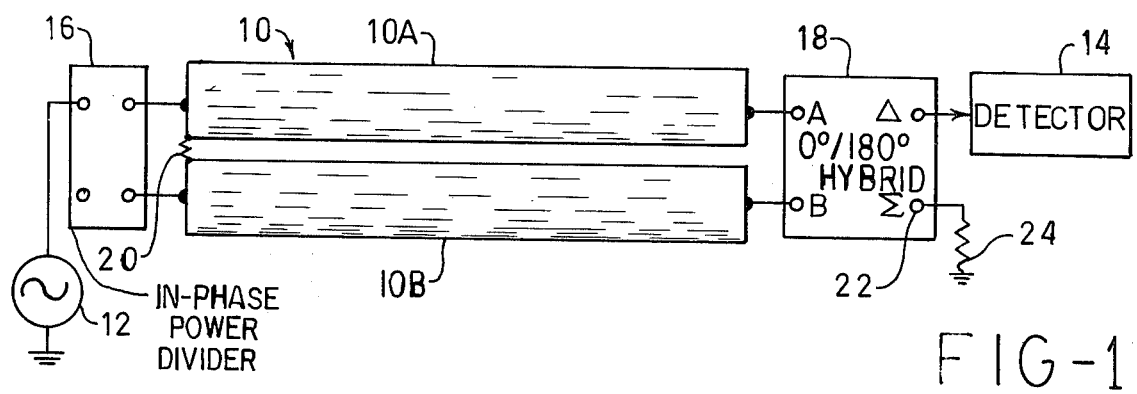
FIG. 1 is a block diagram which schematically shows one embodiment of the flaw detector embodying this invention.

Reference first is made to FIG. 1 wherein the flaw detector of this invention is shown comprising a pair 10 of parallel conductors, or strip transmission lines, 10A and 10B, of equal width. As is well understood, such parallel strip transmission lines are capable of supporting microwave energy of two orthogonal modes, which modes are naturally decoupled. With the present invention, the strip transmission lines are exited with microwave energy of only one mode from a microwave energy source 12, and a detector 14 couples only to an orthogonal energy mode. For purposes of illustration, a matched in-phase power divider 16 is shown for coupling the microwave generator 12 output to the pair of parallel strip transmission lines for excitation thereof in the even mode. In use, the parallel strip transmission lines are located adjacent to and substantially parallel with the test object being inspected for surface flaws, such that the test object serves as a ground plane conductor for return currents. As long as symmetry is maintained, there is no conversion to the odd mode. However, when a surface flaw in the test object perturbs the current adjacent to one transmission line, some power is converted to the odd mode. The detector 14 couples only to the odd mode through use of a sum and difference hybrid (0°/180° hybrid) connecting the other end of the pair 10 of conductors to the detector, the detector being connected to the difference (Δ) terminal, or port, of the hybrid. A resistor 20 connected between the strip transmission lines adjacent the exciting end thereof serves to terminate odd mode signals returned from the opposite end of the lines thereby preventing odd mode standing waves along the line. Similarly, the sum port 22 of the hybrid 18 is connected to ground through a terminating resistor 24 to prevent standing wave even mode signals from developing as a result of a mismatch at the sum port.

With the present arrangement surface flaws along the parallel strip transmission lines are detected, and by relatively moving the flaw detector and test piece generally normal to the strip line axis, large surface areas may be rapidly inspected. This is in sharp contrast to prior art arrangements wherein only spot illumination of the test piece is involved, which requires extensive scanning movement for inspection of large surface areas.

Figure 2A:
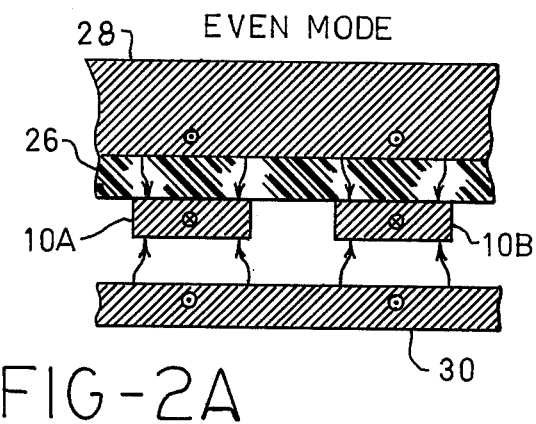
FIGS. 2A and 2B are cross-sectional views of a pair of parallel strip transmission lines showing two orthogonal TEM modes supported thereby for use in explaining the operation of the invention.
Figure 2B:
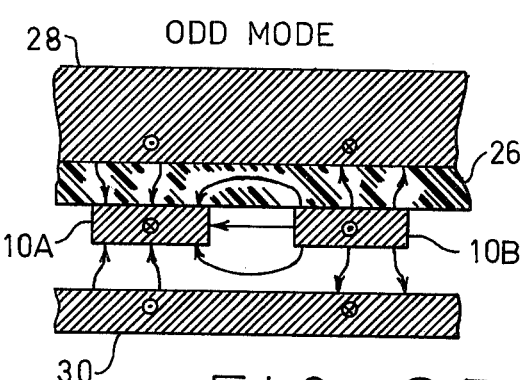

Reference now is made to FIGS. 2A and 2B which show two orthogonal TEM modes supported by the parallel strip transmission lines 10A and 10B. In the illustrated arrangement the conductor pair is shown formed on or attached to a dielectric support 26 affixed to a base 28 comprising a ground plane. Instantaneous electric fields and currents are shown by arrows in the plane of the drawing and arrow heads and tails in a direction normal to the plane of the drawing, respectively. The direction of propagation of the microwave energy along the strip transmission lines is, of course, also normal to the plane of the drawing. An object to be tested for surface flaws is located adjacent to the strip transmission lines 10. For the even mode, shown in FIG. 2A, the two strips are at the same potential with respect to ground. With equal width strips, equal currents in the same direction flow in the two strips. The return currents in the base 28 and test piece 30 are, of course, in a direction opposite to the strip currents. For the odd mode, illustrated in FIG. 2B, the two strips 10A and 10B have potentials, relative to ground, of the same magnitudes, but of opposite polarities. The strips carry equal but opposite currents, and the currents in the base 28 and in the test object 30 (i.e. the ground planes) also flow in opposite directions.

It will be apparent, then, that when the pair 10 of strips is excited in the even mode by generator 12 shown in FIG. 1, there will be no conversion to the odd mode as long as symmetry is maintained. However, when a surface flaw, such as crack, protuberance, or the like, in the test object perturbs the current under one strip but not the other, some power is converted to the odd mode. The incident-mode current excites the flaw, which can be thought of as a virtual current generator required to satisfy the local boundry conditions. The flaw-induced current does not have either type of symmetry shown in FIGS. 2A and 2B, but instead excites both modes. Of particular interest is the coupling to the odd mode, for sensing by the detector 14 which is sensitive only to the odd mode, for flaw indication. It will be understood that the showing of FIGS. 2A and 2B is primarily for purposes of illustrating the two orthogonal modes involved in the operation of the novel flaw detector, and are not drawn to scale. It further will be noted that the flaw-induced current will also couple to a third mode, the parallel-plate mode. This mode has an electric field (not shown) extending between the base 28 and test piece 30 (i.e. from one ground plane to the other) just as if the strips were not present. This parallel-plate mode is not useful for indicating the presence of a flaw because the connections from the strip transmission lines to the generator 12 and detector 14 also excite some parallel plate mode. As will become apparent from a more detailed description of the flaw detector hereinbelow, this mode is suppressed by the use of lossy material located adjacent the strip lines. Also, to avoid higher-order stripline modes, the spacing between the ground planes (base 28 and test piece 30) is only a fraction of a wavelength.

Figure 3:
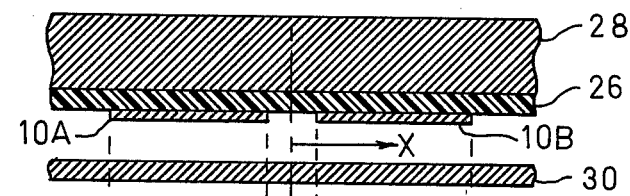
FIG. 3 is a graph showing current distributions for a cross-section of a pair of strip lines, together with a sketch of said cross-section drawn to the same horizontal scale as the graph.
Figure 3:
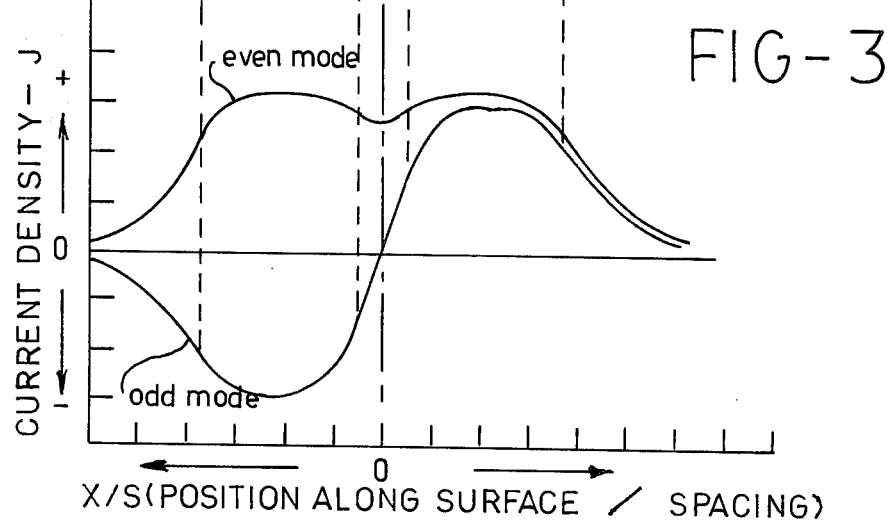

Reference is made to FIG. 3 wherein current distributions for one strip transmission line cross section are shown. At the top of FIG. 3 is a sketch of the cross section to the same horizontal scale as for the curves. The curve of even-mode current has even symmetry about the plane of mechanical symmetry ($X = 0$), and the curve of odd-mode current has odd symmetry about $X = 0$. The spacing between the strip transmission lines is identified by the letter S. The current plots are of the current density J on the surface of the test object 30 vs. X/S (the position along the test object surface divided by the spacing between the strip transmission lines). For both modes in this example, the ground-plane current reaches a maximum within the width of the strip conductors 10A and 10B, and falls off rapidly at positions outside the strip width. Between strips, the even-mode current on the ground plane is only slightly less than its peak value, but the odd-mode current goes to zero at $X = 0$ because of the reversal in current direction for negative X.

As described above, for flaw detection, only one mode (the even mode in the arrangement illustrated) is excited on the strip transmission lines by the generator 12, and the detector 14 is made sensitive only to the odd mode by connection thereof to the strip transmission lines through the difference port of the hybrid 18. Consequently, the detector has zero output as long as symmetry is maintained. A small flaw at a distance X from the plane of symmetry of the strip line couples power into the odd mode. The amplitude of the flaw-coupled signal is proportional to the current density of the even mode at the flaw times the density of the odd-mode current which would exist at that location if the detector and generator were interchanged. Consequently, it will be seen that the product of the even-and odd-mode current densities as a function of the distance X from the plane of symmetry is of greatest interest in the design of a flaw detector incorporating this invention. The coupled signal amplitude is proportional to the product times a polarizability constant that is a function of the crack length, width, and depth.

Figure 4:
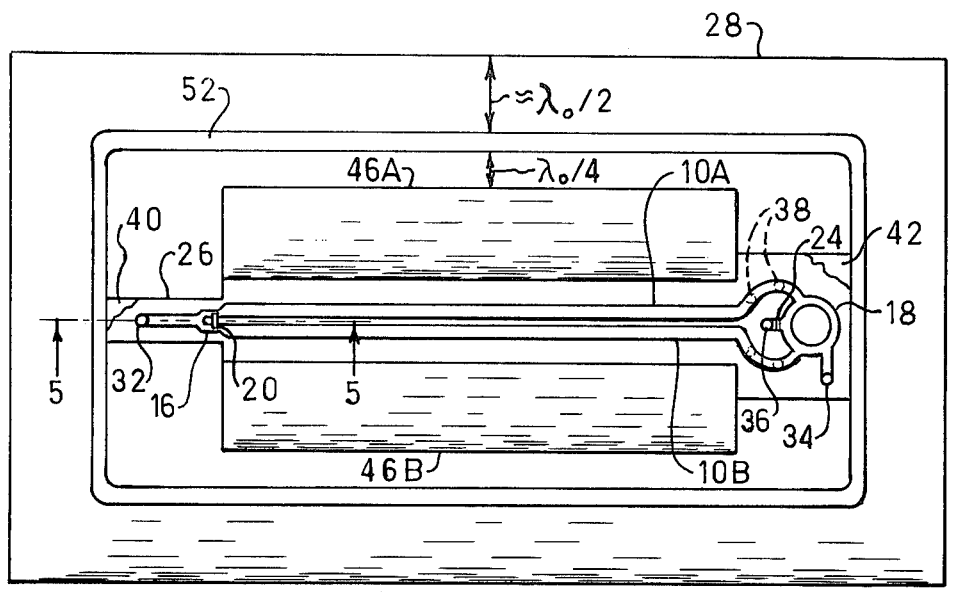
FIG. 4 is a simplified plan view showing a stripline flaw detector of the type shown in FIG. 1 which embodies this invention.
Figure 5:
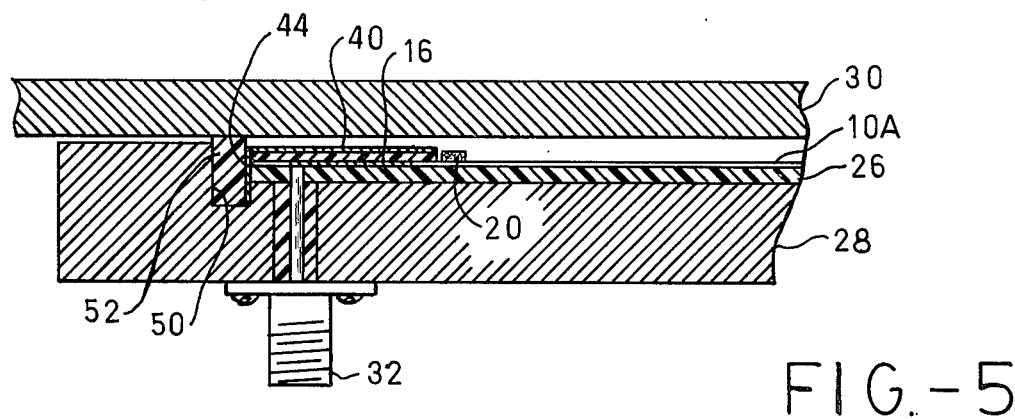
FIG. 5 is an enlarged fragmentary sectional view taken along lines 5—5 of FIG. 4 and showing also a top ground plane covering the power divider.

One embodiment of the above-described invention is shown in FIGS. 4 and 5, to which reference now is made. In the illustrated arrangement the strip transmission lines 10A and 10B, power divider 16 and sum and difference hybrid 18 are shown printed on the support dielectric 26 which, in turn, is affixed to ground-plane base 28. For purposes of illustration, a one-section power divider 16 is shown at one end of the strip transmission lines, which divider has the advantage over a hybrid or other circuits in that it is matched at its design frequency to both the even and odd modes. An input port to the power divider is provided by a connector 32 which extends through the base 28 for connection to the microwave frequency generator 12. A "rat race" hybrid 18 is shown at the opposite ends of the strip transmission lines for coupling to the odd mode. An output port from the out-of-phase arms of the hybrid 18 is provided by a connector 34 which extends through the base 28 for connection to the detector 14. The termination resistor 24 (shown also in FIG. 1) is included in the connection of the in-phase arms of the hybrid to the ground plane at 36. Tuning screws 38 in tapped holes in the ground plane 28 are located along the lines leading to the hybrid from the strip lines to tune the hybrid isolation.

Both the power divider 16 and hybrid 18 are shielded toward the test surface by conductor-clad boards 40 and 42 which overlie the same. In FIG. 4 the shields are shown broken away in order to view the power divider and hybrid. In FIG. 5 the one shield 40 is shown comprising an insulating board which is copper clad along the upper and left end surfaces. Electrical connection of the shield to the ground plane 28 is effected through a conductive strip 44 which extends into groove 50 in the ground plane 28. As seen in FIG. 5, in the vicinity of the transition from the coaxial input connector 32 to the strip-line geometry, connection 44 between the illustrated shield 40 and the bottom ground plane (base 28) is close to the strip to further minimize excitation of the parallel plate mode. The shield 42 (FIG. 4) over the hybrid at the output end of the strip transmission lines is of similar construction and requires no further detailed showing or description.

As seen in FIG. 4 layers 46A and 46B of absorptive material, such as type FGM Eccosorb made by Emerson and Cuming, Inc., Canton, Mass. are located on both sides of the pair 10 of coupled strip transmission lines to dampen out any residual unwanted mode. Damping of undesired modes is essential for proper operation of the flaw detector.

Isolation of the testing line from the ambient area is provided by an R-F choke formed as follows. The small gap between the test piece surface and face of the base 28 adjacent the absorption layers 46A and 46B forms a very narrow, low impedance waveguide. The length of this waveguide is made a quarter wavelength at the operating frequency along the longer sides of the detector. At the ends, this length is $\frac{3}{4}$ wavelength, which is electrically equivalent to $\lambda/4$; the longer length being necessitated by the extent of the power divider 16 and hybrid 18 at the ends. These lengths of low-impedance waveguide are followed by a high-impedance groove 50 formed in the base plate 28, which groove is $\frac{1}{4}$ wavelength deep. The groove 50 is filled with a dielectric member 52 such as polytetrafluoroethylene ('Teflon') or the like, which member extends above the top of the groove a short distance, as seen in FIG. 5. The outer face of the dielectric member 52 engages the test piece 30 and provides a surface for sliding engagement along the surface of the test piece while maintaining a minimum clearance between the test piece and strip transmission lines. With this design the detector ground plane 28 is effectively shorted to the test piece surface.

Figure 6:
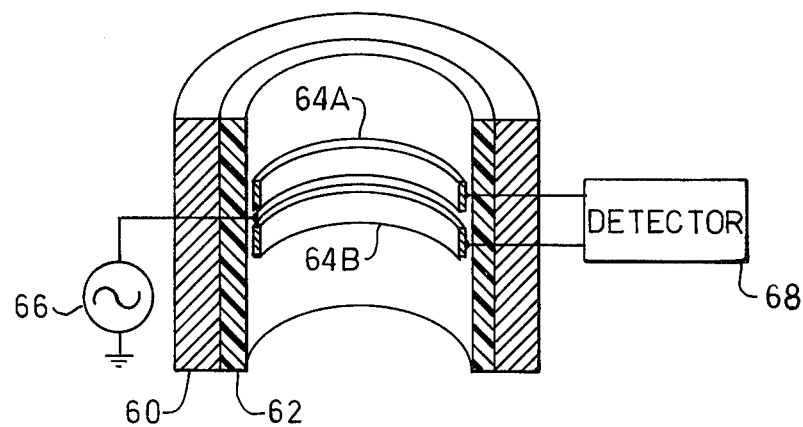
FIG. 6 is a fragmentary perspective view of another embodiment of the flaw detector employing a pair of curved coupled strip transmission lines for inspection of a cylindrical surface.

The invention having been described in detail in accordance with the requirements of the Patent Statutes, various changes and modifications will suggest themselves to those skilled in this art. For example, the coupled strip lines may be curved for the inspection of curved test piece surfaces, and such an arrangement is shown in FIG. 6 to which figure reference now is made. The illustrated flaw detector, which is adapted for inspection of cylindrical metal surfaces, includes a semicylindrical shaped base or housing 60 with a dielectric support 62 on the inner surface thereof for the support of parallel strip transmission lines 64A and 64B. As with the plane surface device disclosed above, the curved strip transmission lines also support orthogonal modes. One end of the lines is supplied with microwave energy from a generator 66 for excitation in only one mode, and detector means 68 is responsive only to an orthogonal mode. Again, the device may be moved along the surface of the cylindrical test object for detection along the surface thereof. In other modified forms of the invention, the coupled strip transmission lines may be formed in a generally spiral shape on the surface of the dielectric support 62. Also, convex rather than the illustrated concave curvature may be employed.

It also will be apparent that the flaw detector may be excited by either one of two orthogonal modes, with the detector responsive to the other mode. For example, the illustrated strip transmission lines may be coupled only to the odd mode from a microwave source and the detector coupled only to the even mode. Also, different power divider means, such as hybrids, and different hybrids may be employed as couplings for coupling the desired modes from the source and to the detector. More than two parallel striplines could also be used with suitable circuitry for coupling to the modes that can propagate thereon. It is intended that the above and other such changes and modifications shall fall within the spirit and scope of the invention as defined in the appended claims.

I claim:
1. Apparatus for detecting flaws at the surface of a test object comprising,
a pair of parallel strip transmission lines,
means for coupling said strip transmission lines to a microwave source for signal propagation therealong of one mode to excite microwave currents on the surface of the test object, and
means coupled to said strip transmission lines for detection of signals of an orthogonal mode produced as a result of perturbations in the excited microwave currents produced by surface flaws.

2. Flaw detecting apparatus as defined in claim 1 wherein said means for coupling said strip transmission lines to a microwave source includes a matched in-phase power divider for supplying the parallel transmission lines with equal even mode signals from the microwave source.

3. Flaw detecting apparatus as defined in claim 1 wherein said means coupled to said strip transmission lines for detection of signals includes a sum and difference hybrid which includes a difference port from which only odd mode signals are obtained.

4. Flaw detecting apparatus as defined in claim 3 wherein said means for coupling said strip transmission lines to a microwave source includes a matched in-phase power divider for supplying the parallel transmission lines with equal even mode signals from the microwave source.

5. Flaw detecting apparatus as defined in claim 4 including shields adjacent to said hybrid and power divider to shield the same from the test object surface.

6. Flaw detecting apparatus as defined in claim 1 wherein said pair of parallel strip transmission lines lie in a plane for inspection of a plane surface on the test object.

7. Flaw detecting apparatus as defined in claim 1 wherein said pair of parallel strip transmission lines are curved for inspection of curved surfaces on the test object.

8. Flaw detecting apparatus as defined in claim 1 including a base comprising a ground plane for the strip transmission lines,
a support dielectric attached to the base and upon which said strip transmission lines are disposed,
microwave absorptive material at opposite sides of the coupled strip transmission lines to damp out unwanted modes thereat.

9. Flaw detecting apparatus as defined in claim 8 including a continuous groove surrounding the strip transmission lines and adjacent absorptive material to provide a high impedance thereat to, effectively, short the ground plane to the surface of the test object.

10. Flaw detecting apparatus as defined in claim 9 including a dielectric in said groove and extending a short distance out of the groove for engagement with the surface of the test object to locate the strip transmission lines in substantially parallel relationship with said surface.

11. A method of detecting surface flaws in a test object comprising,
generating a signal in the microwave range,
supplying said signal to a pair of parallel strip transmission lines for exciting the same with only one mode, locating said strip transmission lines substantially parallel to the surface of the test object, and detecting only orthogonal mode signals produced on said parallel strip transmission lines as a result of surface flaws which couple power between said modes.

12. The method of detecting surface flaws as defined in claim 11 wherein said generated signal couples only to the even mode of parallel strip transmission line propagation and, said step of detecting only orthogonal mode signals includes a detector which couples only to the odd mode.

13. The method of detecting surface flaws as defined in claim 11 wherein said generating and detecting steps operate simultaneously in a continuous operating mode.

* * * * *